United States Patent [19]

Parks

[11] Patent Number: 4,631,125
[45] Date of Patent: Dec. 23, 1986

[54] MIDSTREAM COAL HANDLING APPARATUS

[75] Inventor: Billy W. Parks, Mobile, Ala.

[73] Assignee: Ryan-Walsh Stevedoring Company, Inc., New Orleans, La.

[21] Appl. No.: 716,346

[22] Filed: Mar. 26, 1985

[51] Int. Cl.$^4$ ................................................ B03C 1/00
[52] U.S. Cl. .................................... 209/215; 209/231; 414/138; 414/139; 198/560; 198/563; 198/580; 222/146.6
[58] Field of Search .............. 414/138, 139, 144; 198/560, 563, 580, 588, 543, 544; 73/863.51, 863.52; 34/20; 222/55, 56, 132, 146.6; 209/636, 215, 231

[56] References Cited

U.S. PATENT DOCUMENTS

| | | | |
|---|---|---|---|
| 401,415 | 4/1889 | Conkling | 209/231 |
| 828,316 | 8/1906 | Hulett | 414/138 |
| 2,309,715 | 2/1943 | Rudow | 198/588 X |
| 2,375,487 | 5/1945 | Newhouse | 34/20 |
| 2,982,445 | 5/1961 | Koble | 222/55 |
| 3,009,586 | 11/1961 | Isbrandtsen et al. | 414/144 |
| 3,735,641 | 5/1973 | Bink et al. | 73/863.52 X |
| 3,782,200 | 1/1974 | Maas | 73/863.51 |
| 3,938,676 | 2/1976 | Croese | 414/139 X |
| 3,953,928 | 5/1976 | Novy | 34/20 X |
| 4,106,112 | 8/1978 | Jones | 198/580 X |

FOREIGN PATENT DOCUMENTS

| | | | |
|---|---|---|---|
| 15061 | 5/1956 | Fed. Rep. of Germany | 198/580 |
| 1930041 | 7/1971 | Fed. Rep. of Germany | 222/132 |
| 531237 | 7/1955 | Italy | 198/560 |
| 570400 | 9/1977 | U.S.S.R. | 209/636 |

Primary Examiner—Leslie J. Paperner
Assistant Examiner—Jonathan D. Holmes
Attorney, Agent, or Firm—Keaty & Keaty

[57] ABSTRACT

A midstream apparatus for the receipt, sampling, cooling, and blending of coal provides a continuous transfer capability from one or more barges containing coals of various grades to an ocean vessel requiring blended coal meeting given specifications. The apparatus is a barge mounted combination, having a number of receiving hoppers into which coal may be loaded by transfer from a series of supply barges, usually by a barge mounted clam shell bucket. A number of hoppers are provided so that coal from each barge, having a given specification, may be loaded into a single hopper. Each hopper has individually controlled transfer capabilities permitting the blending of coal of different qualities into a continuous stream. From the hoppers, the coal passes through a magnetic device for removal of iron and then, in a continuous flow along a convoluted, rising belt system which provides, when desirable for diversion of the flowing coal through a series of air drop towers for cooling to maintain the coal with a given maximum temperature. The coal passes a multi-cut sampler for continuous monitoring of blend and quality. The multiplicity of belts raise the coal to a point at which the coal passes via a telescoping transfer belt into an ocean going vessel. The apparatus provides, in compact form, the capabilities of a shorebased storage, sampling, blending and transfer facility and permits the direct transfer of coal from a multiple number of barges onto an ocean going vessel.

7 Claims, 6 Drawing Figures

MIDSTREAM COAL HANDLING APPARATUS

BACKGROUND OF THE INVENTION

1. Field of the Invention

The invention of this application is within the field of hazardous bulk material handling equipment and intermodal materials transfer equipment.

2. General Discussion of the Background

The transportation of coal provides several unique problems not encountered with other bulk commodities. Principal among these problems is the fact that coal, while it is a solid product, is a flammable material. When stored in bulk quantities, it is susceptible to the development of spontaneous combustion, and this tendency is increased if the coal becomes moistened. Gradual temperature rises occur within stored wet coal, and can reach a point, if the quantity of coal is great enough, that the coal will actually catch fire.

This problem is made worse by the fact that coal is a bulk commodity, for which transportation costs are a major portion of the overall economic cost of the use of the product. Thus, coal is often shipped by waterborn commerce, an environment maximizing the problem of moisture and in which large bulk quantities are often accumulated, producing significant combustion hazards.

Coal is a naturally mined product, occuring in a wide variety of grades related to its overall cleanliness, sulphur content, foreign material content (especially shale), and other characteristics having a bearing on the value of the coal for various purposes and thus on its price. As a result, coal is brought to certain quality specifications, depending upon its end use.

Since the coal provided from various mining sources in general either exceeds or falls below the desired quality requirements, it is necessary to blend various coals in order to achieve an overall mixture having the desired properties.

As it is customary that coal is shipped from individual mines in barge load lots, a barge load is typically of a particular quality. This coal is sampled, stored and blended to specification at an intermediate handling facility, usually located for convenience at the point at which the coal is removed from barge or river traffic and transferred to ocean going vessels.

Such shore side facilities are by the nature of the commerce very large, consuming sizeable areas of relatively scarce waterfront land, and imposing significant environmental impact. In addition, the fact that the coal must be transferred from river traffic to ocean going traffic at a fixed location creates major scheduling and access problems as both the barges and the ocean going vessels must be brought to a specific location.

SUMMARY OF THE INVENTION

The present invention provides a barge mounted combination apparatus providing jointly the capabilities to receive, in batch lots, coal having varying characteristics and having various storage temperatures. The apparatus provides a mechanism for blending such coal lots to achieve a given coal quality; it provides the capability of cooling coal so as to maintain it below a desired maximum temperature for further transhipment; it provides a method of periodic or continuous sampling of the coal stream to determine compliance of the blend with the quality specification required; and it provides for a continuous loading onto an ocean going vessel so as to minimize demurrage costs associated with cargo loading of vessels in maritime commerce.

As the entire apparatus provides for all of the essential capabilities of a shore side coal handling facility, it is the purpose of the invention to provide an apparatus which in unified form can provide the intermodal storage, blending, and transfer capabilities of a shore side coal loading complex in a mobile, midstream facility.

The apparatus, being mounted on a barge, by means of the particular combination and arrangement of its material moving elements is fully mobile and thus may be positioned at a point most convenient for the intermodal transfer of coal from a barge to ocean going vessels.

It is thus an object of this invention to provide a mobile intermodal coal transfer facility and capability without restriction to a particular geographic location.

It is a further object of this invention to provide a midstream barge to ocean going vessel coal transfer apparatus which is capable of blending coal from several lots to achieve a uniform characteristic.

Another object of this invention is to provide an intermodal coal transfer apparatus for use between a barge and an ocean going vessel which is capable of maintaining the temperature of the transferred coal below a desired maximum temperature so as to prevent combustion within the ocean going vessel.

Yet another object is to provide an intermodal coal transfer apparatus between a barge and an ocean going vessel which is capable of maintaining a continuous, maximum load rate into an ocean going vessel for the minimization of demurrage charges.

These and other objects of the invention will be more clearly seen in the detailed description of the preferred embodiment and in reference to the figures of the drawings.

DETAILED DESCRIPTION OF THE PREFERRED EMBODIMENT

Figure 1:
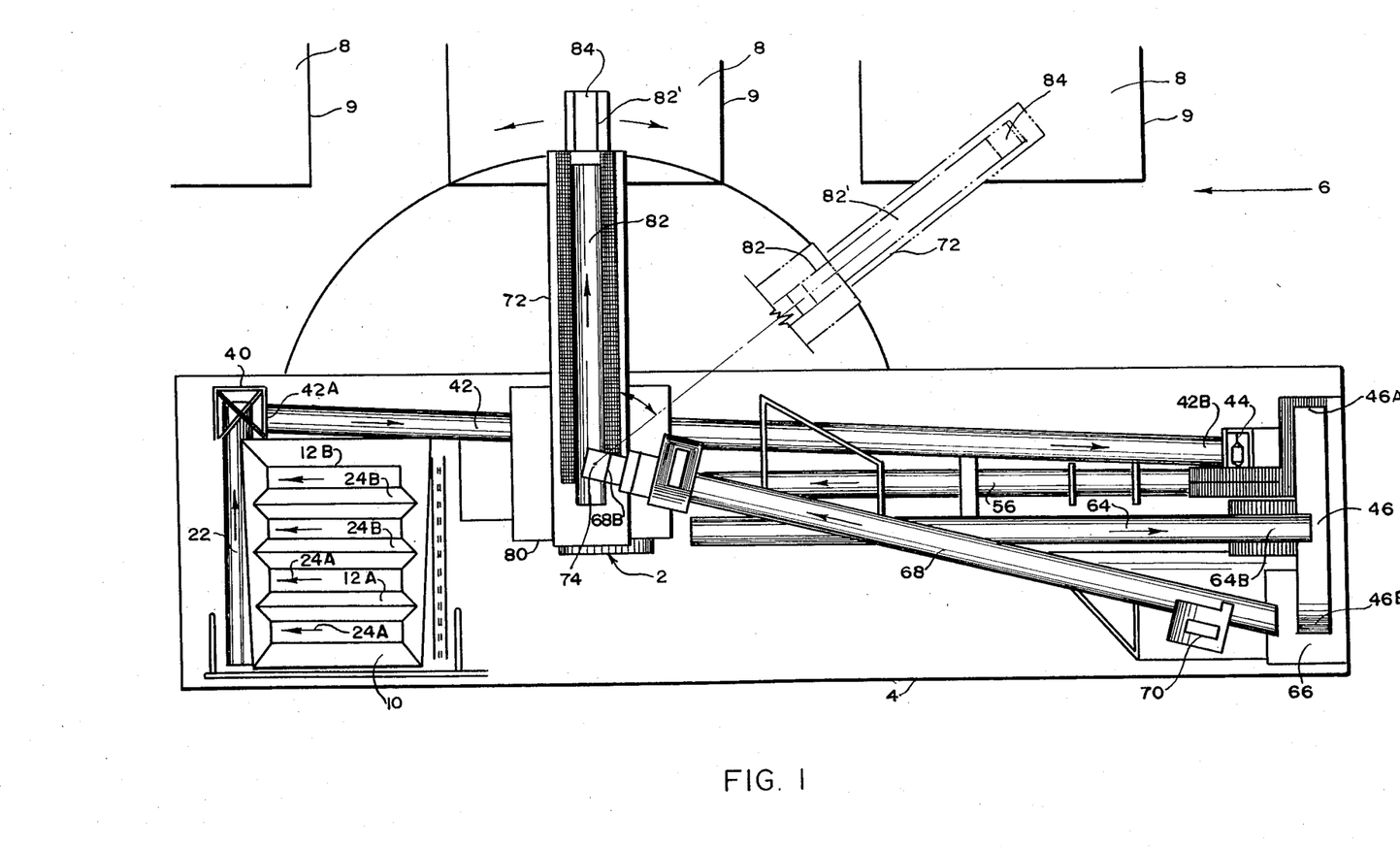
FIG. 1 is a top view of the invention showing the general flow of coal therein, showing in simplified form, the relationship to the holds of an ocean going cargo ship.
Figure 2:
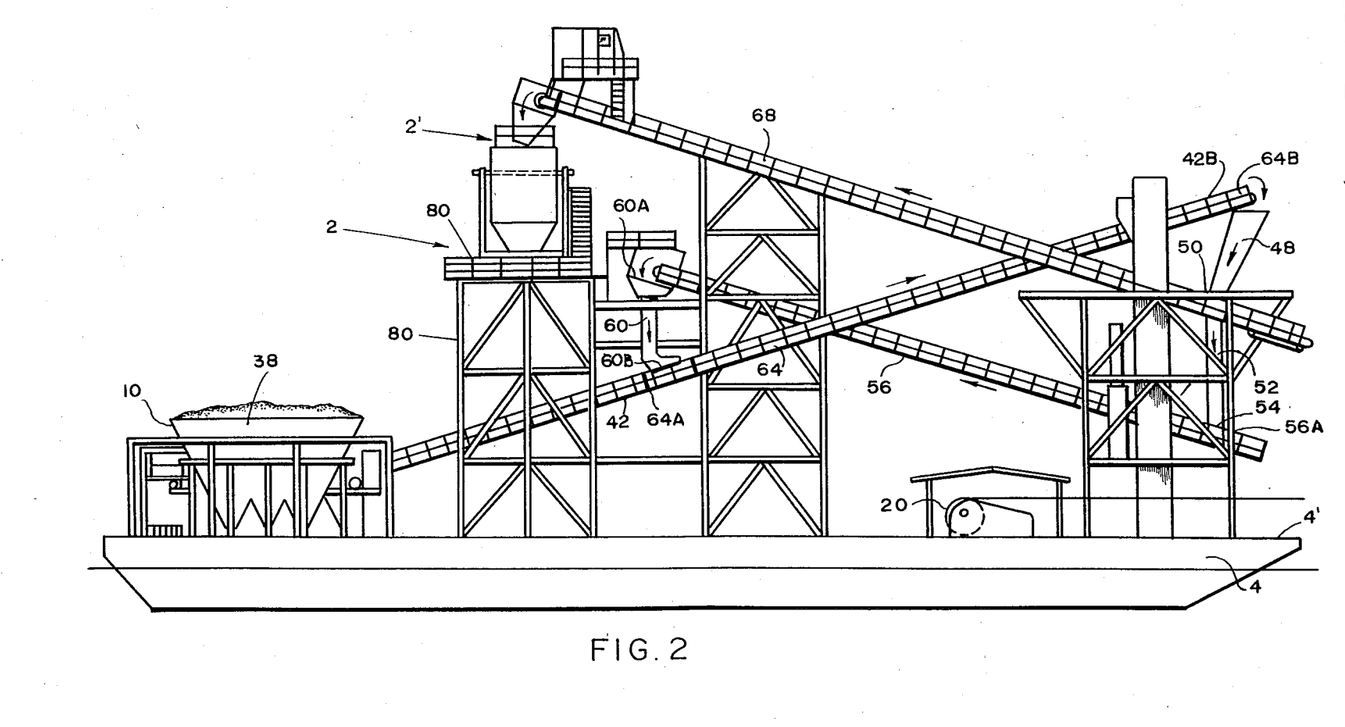
FIG. 2 is a side view of the invention.
Figure 6:
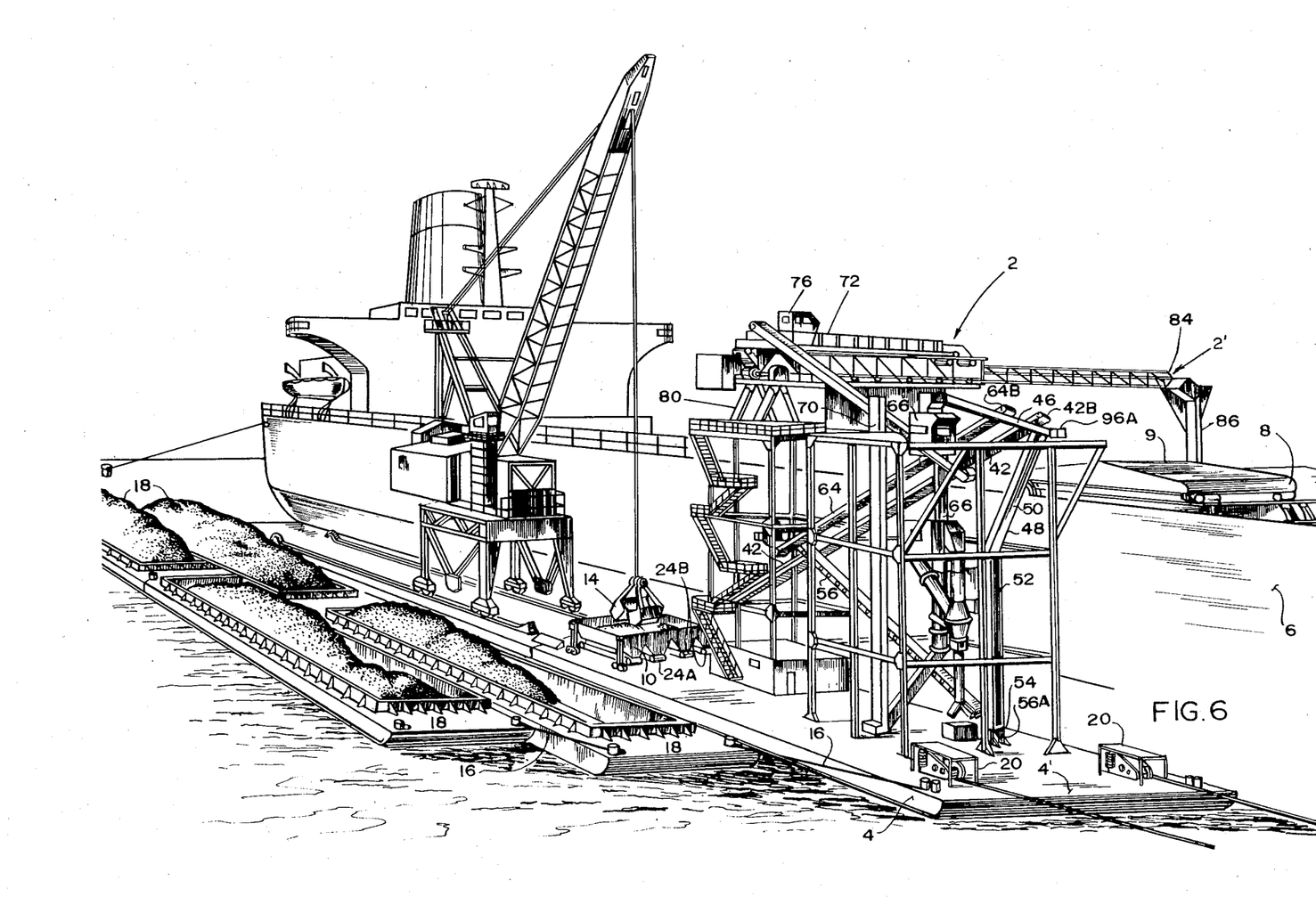
FIG. 6 is a perspective view of an earlier conception of the invention showing the interrelation of a coal barge, clam shell shovel, invention, and ocean going vessel.

The invention may best be understood by referring to FIG. 1 in conjunction with FIG. 6. It should be understood throughout this discussion that FIGS. 1 through 5 disclose the preferred embodiment of the invention while FIG. 6 discloses an earlier, less preferred conception. FIG. 6 is, however, included for the understanding of the interrelationship of the invention as disclosed herein with the environment in which the invention is used.

As shown in FIG. 1, the apparatus 2 of the current invention is seen to be mounted upon a barge 4 of size and configuration for riverborn traffic. Such barges 4 are found throughout the inland waterways of the United States and are well known to the art. In this case, the barge 4 provides a buoyant floating platform upon which the apparatus 2 of the present invention is erected as will be hereinafter disclosed. FIG. 1 shows in figurative form the barge 4 adjacent to a ship 6, depicted for clarity in FIG. 6 and shown in FIG. 1 by means of the various holds 8 identified by their hatch openings 9.

The barge 4 in typical practice will be 196 feet long by approximately 54 feet wide and will, under normal loading, draw approximately a 7 foot draft in fresh water. As may be seen from FIG. 6, the uppermost level 2' of the apparatus 2 must clear the hatches an ocean going vessel and it is found that the top of the apparatus 2 will be at least 80 feet and may preferably be approximately 88 feet above the barge deck.

Referring to FIG. 1, the overall apparatus 2 may be seen in more detail to include a hopper assembly 10 having two pairs of hoppers, 12a and 12b. Each of the hopper pairs 12a and 12b are adapted for the receiving of coal from a barge mounted clam shell bucket 14 as shown in FIG. 6. Such a barge mounted clam shell bucket is well known in the art and need not be described further. It should be noted that in general practice, the barge containing the clam shell bucket 14 is adjoined to the barge 4 of the current apparatus, being linked together by means of cable and mooring point as is known in the maritime art so that the crane barge and the barge for the current invention operate as a unit.

Again referring to FIG. 6, it will be seen that alongside barge 4 are a plurality of standard open barges 18 containing coal, the barges 18 being moored together by cables 16. In an identical manner, not shown, barge 4 is moored to ocean going vessel 6. Barge 4 is provided with anchor winches 20 (see FIG. 2), by which it may be moored in a standard manner to a midstream mooring point or anchoring point, not shown.

The apparatus of the present invention, as mounted upon barge 4, continues from the hopper assembly 10, by means of a lateral transfer conveyor 22 which receives coal from hopper conveyors 24a and 24b, located respectively along the bottom of each of hoppers 12a and 12b, for transferring coal from each hopper.

Hopper conveyors 24a and 24b, as all conveyors herein, are standard endless belt conveyors, of flexible reinforced material, and run, as is known in the art, preferably upon tapered rollers so as to provide a slight troughing or concave effect, so as to tend to resist the spilling of coal from the sides of the conveyors. In the preferred embodiment of the invention, each of the conveyors hereinafter mentioned is also equipped with flexible wiping rubber side skirts extending vertically from a point above the outer edges of each of the conveyor belts down to and wipingly contacting the edges of each of the conveyor belts. These side wipers, not shown, are found to aid in eliminating the spillage of coal particles during the movement of each of the conveyor belts.

All conveyors described hereinafter have certain common design features which are not shown in the drawings for clarity, and which are considered to be within the common design art for conveyors. Each conveyor is a continuous loop belt conveyor. The telescoping conveyors 82 have longitudinal grooving; the remainder have smooth surfaces. Each conveyor has independent power drive means, either explosion proof electric or hydraulic; each is capable of independent control. The controls for the belts are interconnected so that an operator in cab 76 may activate or stop any belt. In addition, the controls are interconnected so that stoppage of any belt will also stop any belt feeding coal in the described flow pattern prior to the stopped belt, to prevent build up and spillage. At any point along the apparatus, such as catwalks, where an operator or crew member may be adjacent to a belt, emergency control access is provided to enable shutdown of movement.

Figure 3:
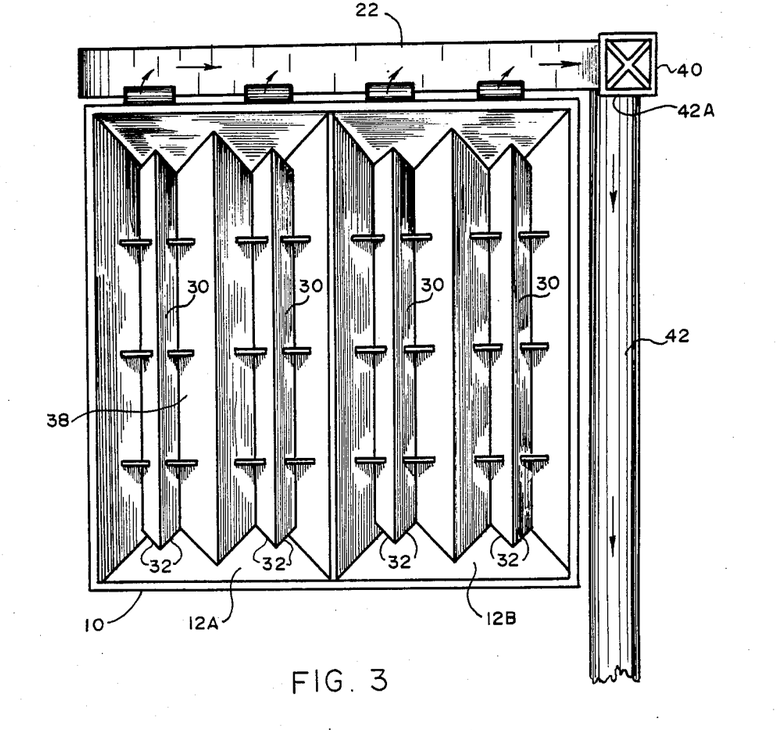
FIG. 3 is a top view of the receiving hoppers of the invention.
Figure 4:
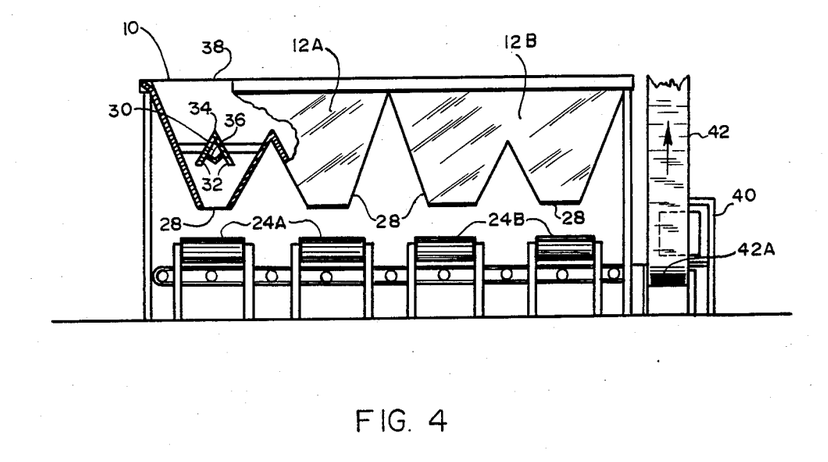
FIG. 4 is an end view of the receiving hoppers of the invention with a section cut away showing the interior arrangement thereof.
Figure 5:
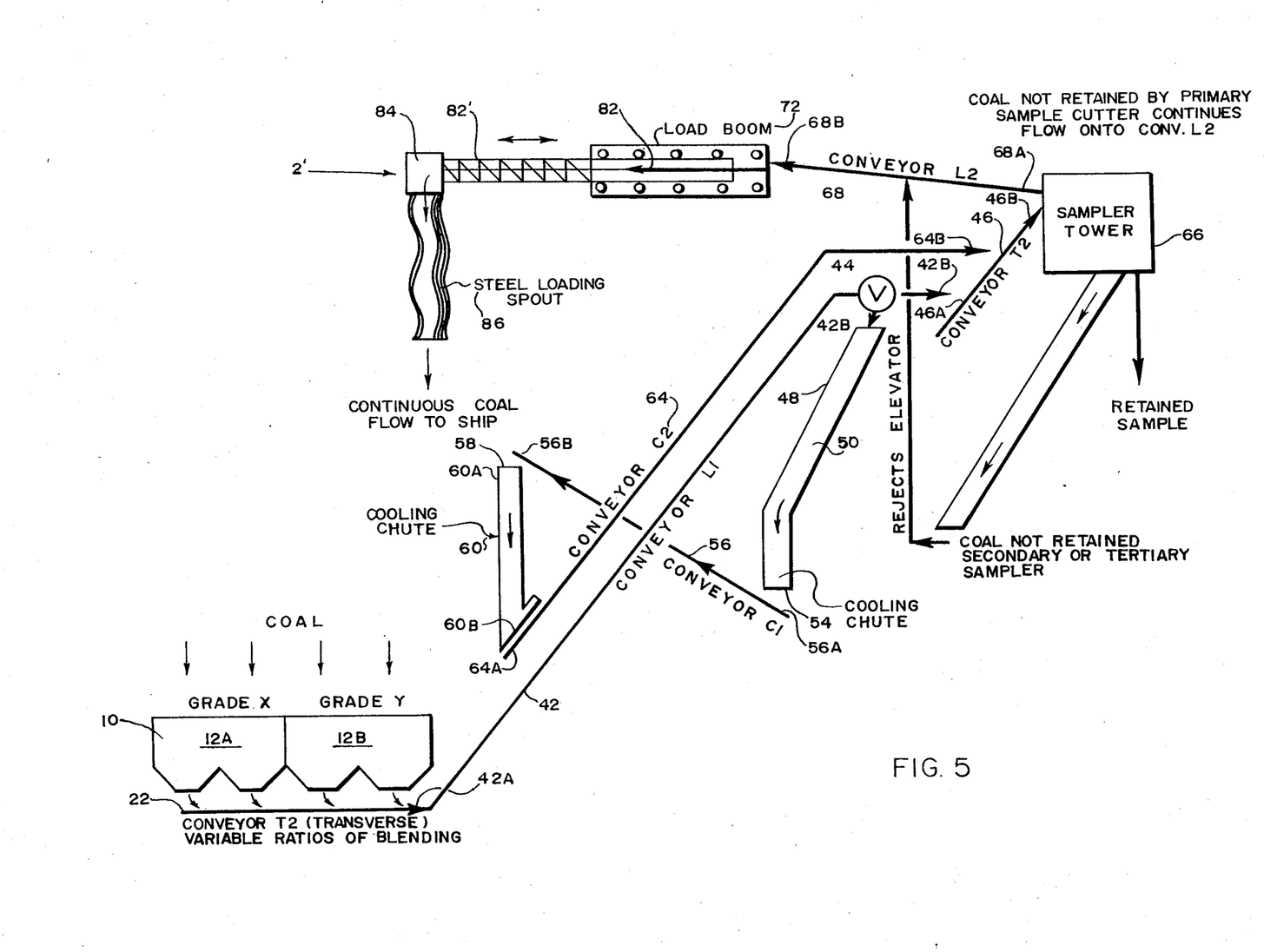
FIG. 5 shows a diagram of the alternative control coal flows within the invention.

FIGS. 3 and 4 in combination show greater detail of the construction of hopper 10. Hopper 10 and the two individual hopper pairs, 12a and 12b, contained therein comprise a generally elongate receiving structure having openings or bottom ports 28.

A simple gate is located at the discharge end of each feeder conveyors 24a and 24b to control height of flow of coal being conveyed by conveyors 24a and 24b to transverse conveyor 22. The bottom port 28 is located vertically above the individual hopper belts or conveyors 24a and 24b.

Hopper 10 is preferably designed so as to present a relatively large open aspect at its top 38, thereby providing a large target area in order to ease the efforts of the crane operator as he places the bucket 14 over the individual hoppers 12a or 12b.

Further, the vertical height of the hopper 10 is designed deliberately to have as low as feasible a profile so that minimum hoisting of the bucket 14 is required to reduce the overall distance and motion required of the clam shell crane.

Each of the conveyor belts 24a and 24b, being as described above continuous conveyors, have individual power means not shown. The direction of each of the belts 24a and 24b is such that material thereupon is passed to lateral transfer conveyor 22. Lateral transfer conveyor 22 passes under magnetic scrap remover 40, which in the preferred embodiment is a large electromagnet mounted directly over transfer conveyor 22. Transfer conveyor 22 moves in a first direction, ending immediately above a receiving end 42a of first longitudinal conveyor 42 which is substantially perpendicular to conveyor 22. First longitudinal conveyor 42 extends from a first end of barge 4 adjacent magnetic scrap remover 40 along the long dimension of barge 4 to a second end of barge 4 (see FIG. 1).

In this transit, first longitudinal conveyor 42 rises at an angle of approximately 17.5° maximum. This angle is based upon the natural angle at which coal will spill back upon itself, the so-called angle of repose, which is approximately 18°. This angle, as is well known, represents the maximum angle of rise for particulate coal being conveyed on a frictional belt. As the angle is increased beyond this angle, coal will spill back down the belt rather than travelling along it. The angle of longitudinal conveyor 42 is chosen about ½ degree less than the angle of repose, to allow for normal heave and pitch motions of the barge in a riverway while maintaining the coal at an angle below the critical angle aforesaid.

At the upper delivery end 42b, immediately beneath end 42b is found first diverter valve 44. First diverter valve 44 is essentially a triangular receiving structure fully enclosed containing therein a gate valve, not shown, which is actuatable between a first and a second position. Said first position provides gravity passage of coal to a receiving end 46a of a second lateral transfer conveyor 46. Said second position of diverter valve 44 permits gravity flow of coal into cooling tower 48 (see FIG. 5 for schematic diagram). Cooler tower 48 is a vertical, gravity fall, enclosed chamber having a first angular descent portion 50 and a second more vertical descent portion 52. Cooling tower 48 is an enclosed tower permitting the free gravity fall of particles of coal and simultaneously adapted to the free vertical flow of air about said coal. The vertical direction of cooling tower 48 defines a lower exit 54 immediately above a receiving end 56a of second longitudinal conveyor 56. Second longitudinal conveyor 56 extends from a lower position 56a immediately beneath lower exit point 54 in a direction substantially longitudinally along the long axis of barge 4, at an angle of climb approximately the same as that of first conveyor 42, but having an end 56b, terminating at a point 58 approximately midway, in a vertical direction, between the lower end 42a of said first conveyor 42 and the upper end 42b of said first conveyor 42. At this midtermination point 58 is found a second substantially vertical cooling tower or chute 60, again comprising an enclosed vertical tower having an upper end 60a for receiving particulate coal from said conveyor 56 and adapted to the gravitational fall of said coal to a second lower end 60b. Lower end 60b is provisioned for flow, by gravity, of coal onto a receiving end 64a of third longitudinal conveyor 64.

Third longitudinal conveyor 64 is a vertically ascending conveyor of an angle and design equivalent to that of second conveyor 60 and first longitudinal conveyor 42. Conveyor 64 ascends from a coal receiving end 64a beneath tower end 60b to a delivery end 64b immediately above second lateral transfer conveyor 46, the upper end 64b of conveyor 64 being adapted for gravity fall of coal onto second lateral transfer conveyor 46.

The combination of first cooling tower 48, second longitudinal conveyor 56, second cooling tower 60, and third longitudinal conveyor 64 are referred to hereinafter as the cooling loop.

Second lateral transfer conveyor 46 extends from a point adjacent first diverter valve 44 to a second point adjacent the top of sampler tower 66. Sampler tower 66 comprises a bucket sampler design known in the art, having a largely open gravity chute, not shown, extending from an end of lateral tranfer conveyor 46 to a receiving end of final longitudinal conveyor 68. Within sampler tower 66, a diverter gate be periodically actuated to divert a quantity of coal from sampler tower 66. Within sampler tower 66 is found a three cut automatic mechanical sampler of design known in the coal industry for preparing samples according to the specifications set by the American Society for Testing and Materials. In general, each such sampler, in a manner well known to the art, proceeds from a first cutter, or variable gate which diverts some coal from the flow between transfer conveyor 46 and final longitudinal conveyor 68 so as to remove a sample quantity of coal. Said sample then flows gravitationally within sampler tower 66 through a crusher which reduces it to a fine particulate state and through mechanical dividers, usually in two stages, which serve to pull a small quantity of the crushed particulate coal for testing purposes. As is well understood, the combination of the agitation provided by the two vertical cutters on the fine particulates coal intermixes the particulate so as to produce a uniform homogeneous sample.

The internal construction of the sampler tower is understood in the coal sampling art to be standard, even though for each particular installation manufacturers will provide a range to fit a given gravitational fall tower. In particular, for the preferred embodiment given herein, the first or primary cutter within the tower is a Redding-Wilmont Type C primary cutter as provided by the James A. Redding Company of Pittsburgh, Pa. The secondary cutter is a Wilmont Type C secondary cutter also provided by the James A. Redding Company. The crusher is a Jeffrey Model 30AB pulverizer set for a 95% 8 mesh product and a final sampler is a Wilmont DTS-200-60 unitized sampler also provided by the James A. Redding Company.

Sampler 66 is preferably configured to sample from a designed 2400 tons per hour flow rate for coal along the conveyor belts 46, 68. The sampler is a conventional three cut sampler as described. The first cut pulls approximately 30 samples per hour, of about 889 pounds per sample. This first sample is then sampled in a second cut, taken 180 times per hour, of about 15.86 pounds per sample. This second sample cut is then crushed to an approximate size of 4 mesh size particles and then sampled at a rate of about 100 cuts per hour, with each cut being about 0.055 pound.

That portion of the coal not utilized in the final sample 26,670 pounds per hour, less 5.5 pounds per hour) is returned to the coal flow on conveyor 68 by sample return elevator 70. Elevator 70 is, in this embodiment, a Link-Belt (tm) Model 147 centrifugal discharge elevator rated at 13.33 tons per hour lift capability. Any equivalent capacity bucket belt lift elevator would be suitable for the purpose.

The sampler 66 described above is designed to meet American Society for Testing and Materials (ASTM) specifications designation D-2234 "STANDARD METHOD FOR COLLECTION OF A GROSS SAMPLE OF COAL" and designation D-2013 "STANDARD METHOD OF PREPARING COAL SAMPLES FOR ANALYSIS".

It will be understood by those skilled in the art that the cutters and samplers specified are in fact internally provided with individual belts and chutes, but all are mounted internally in a well understood manner within sampler tower 66 so as to provide a homogeneous sample at a lower end of tower 66.

Final longitudinal conveyor 68 extends from sample tower 66 whence it conveys the majority of the coal provided the sampler tower 66 to a delivery end 68b above telescoping boom 72.

Telescoping load boom 72 as shown in FIG. 1 and FIG. 6 is a pivoting boom having a control cab 76 (FIG. 6) mounted adjacent to and above a pivot point 74 (FIG. 1). This pivot point 74 is a point of receiving coal from final conveyor delivery end 68b. The entire load boom 72 pivots about point 74, and is supported on a large thrust bearing (not shown) which couples the load boom 72 into vertical support structure 80 mounted to top barge 4.

Cab 76 contains controls adapted to rotate load boom 72 about pivot point 74. Load boom 72 comprises telescoping sections 82 and 82'. Cab 76 contains controls for extending telescoping sections 82 and 82' with respect to each other. Load boom 72 extends from pivot point 74 to delivery end 84. Delivery end 84 is provided with a dust chute 86 extending downwardly therefrom, adapted for the suppression of dust from the fall of coal from the delivery end 84 of load boom 72.

In operation, an operator aboard the barge mounted crane activates and operates crane clam shell bucket 14 so as to transfer coal from the alongside barges 18 into one of hoppers 12a or 12b. It will be understood that such coal will have had an initial sample to determine its basic characteristics. Thus, it is well understood from the characteristics of the coal in the barges 18, the relative proportions of each lot of coal in hoppers 12a and 12b, which, when intermixed, will make up a desired quality of coal.

Thus the relative speeds of belts 24a and 24b are set so that they will transfer, in proportion to the desired mix, coal from each of their respective hoppers 12a and 12b onto first lateral transfer belt 22.

First lateral conveyor belt 22 then conveys the admixed coal past magnetic scrap remover 40, which serves the purpose of removing any ferrous scrap items which might be in the coal and which might damage the operation of sampler 66. The coal is then transferred by gravity fall from end 22b to end 42a of first longitudinal conveyor 42; conveyor 42 serves the primary purpose of raising the coal to a height sufficient for gravitational flow of coal as required, either into the cooling loop aforesaid, into sampler tower 66 or onto the final longitudinal conveyor 68 for providing coal to the load boom 72.

It should be understood that the angle, design, and length of longitudinal conveyor 42 is somewhat critical, as the maximum angle of inclination, based on the angle of repose of coal, when viewed in light of the 88 foot vertical lift desirable on the 196 foot long barge, provides a limiting factor in the design of the apparatus. The particular combination and interrelationship of conveyors shown herein has been found to achieve the necessary vertical rise of coal within the dimensional constraints of standard barge sizes while not exceeding the maximum lift angle. It is important in this regard to remember that, in as much as the apparatus 2 is mounted upon a floating barge 4, an additional tolerance must be allowed for pitch and roll of the barge under expected river conditions.

If it has been determined that when the coal being provided from the various barges has built up an excessive temperature and therefore presents a danger of spontaneous combustion, then the coal flow being raised on first conveyor 42 is diverted by first diverter valve 44 into the cooling loop, comprising vertical descent cooling tower 48, longitudinal conveyor 56, second cooling chute 60 and longitudinal conveyor 64. The combination comprising said cooling loop provides sufficient exposure to cooling air to individually cool the particles of coal.

The break in descent in first cooling tower 48 created by having a first angular descent portion 50 and then a second more vertical descent portion 52 provides sufficient vertical fall in air for cooling yet prevents serious mechanical damage to the coal from an excessive vertical drop. The overall combination of free fall through air plus the open exposure to cooling air while travelling on conveyors 56 and 64 sufficiently cools the coal so as to essentially remove all danger of spontaneous combustion.

The coal from first conveyor 42, whether or not diverted by the diverter valve 44 into the cooling loop, is then transferred by lateral transfer conveyor 46 to sampler tower 66. As stated within the description of sampler tower 66, a sampling cutter removes a small portion of the coal at periodic intervals for crushing, mixing and sampling. The remainder of the coal is provided, through gravity fall from delivery end 46b of lateral conveyor 46 onto a final longitudinal conveyor 68, which, doubling back over first longitudinal conveyor 42, provides within the overall length of the barge 4 a sufficient vertical rise so that the final coal level 2' is above the deck height of ship 6 and thus is positioned for final lateral transfer for continuous loading.

Throughout, as stated above, each of the conveyors from first lateral conveyor 22 through final longitudinal conveyor 68 are essentially concave cross section belt conveyors. Further, in order to provide a continuous flow of coal without accumulation of localized build ups, each conveyor is run at essentially the same speed in terms of linear feet per minute of conveyor travel. Each conveyor is individually powered, in the preferred embodiment by a combination of electrical and hydraulic motors. For purposes of safety, the electrical control system, not shown in the drawings, is a conventional one but is wired so that the emergency shut down of any conveyor in the sequence given above will shut down all conveyors feeding coal up to the point of shut down but will leave those conveyors between the point of shut down and the load boom functioning. This safety precaution prevents the accumulation and spillage of coal in the event it is necessary to shut down one or more of the conveyors for any reason.

The aforesaid sequence of conveyors, terminating in final loop conveyor 68, provides coal at a certain rate to pivoting load boom 72. Load boom 72 is a telescoping boom positioned by an operator located within cab 76 so that the distribution chute or loading spout 86 may be transitioned evenly across and around each of holds 8 of ship 6 so as to provide a uniform continuous load of coal into ship 6. It will be seen that in transitioning between holds 8 of ship 6, it will be occasionally necessary to delay or temporarily stop the flow of coal from load boom 72. At the same time, in as much as load boom 72 is in fact telescoping conveyor sections 82 and 82', it may be apparent that the telescoping movement of sections 82 and 82' with respect to each other might produce an excessive flow of coal onto the second 82' conveyor. In order to prevent such accumulations the coal and to eliminate the possibility of spill, the conveyor belts on load boom 72 are designed to run at a speed faster than that of conveyors 68 and conveyors feeding it. This differential speed also reduces the total weight of coal upon telescoping conveyors 82, 82', thus reducing the total upsetting moment imposed upon pivot 74 and barge 2 from the asymmetric position of boom 72.

Furthermore, in the preferred embodiment of the invention, the conveyor belt of load boom 72 has a faster running speed to cause the coal flow upon boom 72 to be narrower and more centralized than the flow arriving along final conveyor 68. The higher speed of the conveyors on boom 72 prevents accumulation of excessive coal build up during the movement and transitioning of boom 72.

It may be necessary upon cessation of loading in one hold 8 to temporarily stop the flow of coal as the boom is transitioned to a second hold 8. The operator in cab 76 is thus provided controls (not shown) enabling him to start and stop transfer by stoppage control of all conveyors including the conveyors in hoppers 12a and 12b.

The apparatus 2 can thus be seen to combine in a single midstream floating apparatus the capability to use automatic mechanical sampling for full satisfaction of American Society for Testing and Materials specifications, where only hand sampling was formerly available in the midstream coal loading art. This capability formerly has only been available in large land base terminals.

Further, apparatus 2 provides a blending capability of greater sophistication than that found even in most land base terminals inasmuch as it provides for a continuous blending for multiple stocks during continuous ship loading. The apparatus in the preferred embodiment of the invention has the capability for blending of two grades of coal in accurate proportions or ratios from one to one up to four to one, and at even greater ratios at lower throughput rates.

The apparatus 2 attacks the problem of spontaneous heating and combustion by providing an adequate cooling loop within the physical confines of a midstream barge. The apparatus disclosed above has approximately 600' of belt conveyor with six transfer points and the cooling loop adds approximately 150' with a vertical air cool drop greater than the vertical height of the apparatus concerned.

In summary, the concept of midstream transfer, blending, sampling, and cooling is unique and provides capability heretofore only seen in large land based installation. It provides a capability for midstream loading and coal transfer operations having all of the capabilities of a land based terminal. The apparatus can transfer coal or in combination with transferring coal can provide one or more or all of the functions of blending, sampling and cooling.

It can thus be seen that the combination provides capabilities not available in the prior art and which prior to this disclosure would not have been considered feasible in a midstream transfer unit.

I claim:

1. An apparatus for the loading of coal upon ocean going vessels comprising:
   barge means for supporting the apparatus upon a deck thereof;
   receiving means mounted at a first level upon said barge for receiving coal;
   continuous movement means mounted on said barge, connected to said receiving means, for establishing a flow of and raising said coal to a second, higher level;
   means mounted on said barge for receiving said coal at said second level, adapted to divert said coal to a first or a second alternative flow path,
   said first flow path being adapted to cool said coal and to convey said coal to said second flow path,
   said second flow path being adapted to move said coal to a sampling position;
   sampling means mounted on the barge at said sampling position for extracting a sample of said coal periodically from the flow; and
   positionable means for receiving said flow of coal, adapted for delivering said flow of coal to a plurality of positions within an ocean going vessel.

2. The apparatus as described in claim 1 above, wherein said receiving means comprises:
   a plurality of hoppers, having substantially wide receiving openings adapted to receive coal;
   conveyor means for removing coal from said hoppers at a determinable rate and;
   means for blending coal from each hopper in a determinable ratio.

3. The apparatus as described in claim 2 above further comprising:
   winch means, affixed to said barge means, adapted for securing and moving said apparatus alongside and with respect to an ocean going vessel.

4. The apparatus as described in claim 3 above further comprising:
   magnet means, for removing ferrous foreign matter from said coal, mounted on said barge adjacent said flow of coal.

5. The apparatus as described in claim 4 above, wherein said first alternate flow path comprises:
   a first, gravity fall cooling tower extending from the second level to an exit point adjacent the deck of said barge;
   first lifting conveyor means extending for movement of coal from said exit point to a mid-height level;
   a second, gravity fall cooling tower extending from said mid-height level to a lower second exit; and
   second lifting conveyor means extending for movement of coal from said lower second exit to a point adjacent the second alternate flow path, adapted for flow of coal onto said second flow path.

6. The apparatus as described in claim 5 above wherein said positionable means comprises:
   feed conveyor means for conveying said flow of coal from the sampling means to a point of a pivot means supported atop said barge;
   telescopic conveyor means pivotally mounted for radial movement about said pivot means, said telescopic conveyor means further comprising:
   a first and a second load conveyor means mounted for telescopic movement with respect to one another;
   said first load conveyor means being adapted for receiving said flow of coal at said point of said pivot means;
   said second load conveyor means receiving said flow of coal from said first load conveyor means and conveying said flow of coal to an end of said second load conveyor for gravity flow delivery of coal; and
   means for positioning of said end over a receiving hatch of an ocean going vessel.

7. The apparatus as described in claim 6 above, wherein said first and second load conveyor means are adapted for movement of coal at a rate faster than the rate of flow along the feed conveyor means.

* * * * *